US010251970B1

(12) United States Patent
Bullard et al.

(10) Patent No.: US 10,251,970 B1
(45) Date of Patent: Apr. 9, 2019

(54) AIR SANITATION APPARATUS FOR FOOD PROCESSING TANKS HAVING AIR AGITATION PIPING AND METHODS THEREOF

(71) Applicant: Zee Company, Chattanooga, TN (US)

(72) Inventors: Robert C. Bullard, Signal Mountain, TN (US); Battle Glascock, Soddy Daisy, TN (US); James A. Faller, Chattanooga, TN (US); Jonathon R. Bullard, Chattanooga, TN (US)

(73) Assignee: ZEE COMPANY, Chattanooga, TN (US)

( * ) Notice: Subject to any disclaimer, the term of this patent is extended or adjusted under 35 U.S.C. 154(b) by 280 days.

(21) Appl. No.: 14/978,514

(22) Filed: Dec. 22, 2015

Related U.S. Application Data

(60) Provisional application No. 62/097,951, filed on Dec. 30, 2014.

(51) Int. Cl.
| *A61L 9/20* | (2006.01) |
| *A23L 3/00* | (2006.01) |
| *A22C 21/00* | (2006.01) |
| *A61L 9/14* | (2006.01) |

(52) U.S. Cl.
CPC .......... *A61L 9/205* (2013.01); *A22C 21/0061* (2013.01); *A23L 3/001* (2013.01); *A61L 9/14* (2013.01)

(58) Field of Classification Search
CPC .................................. A61L 9/14; A61L 9/205
See application file for complete search history.

(56) References Cited

U.S. PATENT DOCUMENTS

| 8,168,122 B2 | 5/2012 | Lee |
| 8,685,329 B2 | 4/2014 | Lee |
| 2004/0005338 A1 | 1/2004 | Bachmann et al. |
| 2005/0186124 A1* | 8/2005 | Fink ........................ A61L 9/205 422/121 |
| 2006/0104858 A1* | 5/2006 | Potember ................ A61L 9/015 422/4 |

(Continued)

FOREIGN PATENT DOCUMENTS

| EP | 2 647 716 A1 | 10/2013 |
| EP | 2 647 717 A1 | 10/2013 |

(Continued)

OTHER PUBLICATIONS

Spencer et al., APCI 2011 Annual Educational Conference & International Meeting, Jun. 27-29, 2011, 67 pages.

(Continued)

*Primary Examiner* — Sean E Conley
(74) *Attorney, Agent, or Firm* — Patterson Thuente Pedersen, P.A.

(57) ABSTRACT

An air sanitation apparatus capable of providing an antimicrobial agent in the form of a gas or mist into the air lines that feed into a processing tank for air agitation of the contents in the processing tank, the air sanitation apparatus capable of being operably coupled to an air supply header that uses a plurality of air supply tubes connecting the air supply header. The source of compressed air passing through the air sanitation apparatus having a microbial load decreased using photohydroionization and the antimicrobial agent.

21 Claims, 5 Drawing Sheets

(56) References Cited

U.S. PATENT DOCUMENTS

2006/0229225 A1* 10/2006 Martin .................. A01N 37/16
                                                              510/375
2011/0070267 A1   3/2011 Bachmann et al.
2013/0055471 A1   2/2013 Holman

FOREIGN PATENT DOCUMENTS

WO   WO 2004/000351 A1   12/2003
WO   WO 2011/074959 A1    6/2011
WO   WO 2014/052378 A2    4/2014

OTHER PUBLICATIONS

Boyce et al., "Terminal Decontamination of Patient Rooms Using an Automated Mobile UV Light Unit", Infection Control and Hospital Epidemiology, Aug. 2011, vol. 32, No. 8, pp. 737-742.

Čeřovský, et al., "Inactivation of Possible Micromycete Food Contaminants Using the Low-Temperature Plasma and Hydrogen Peroxide", Plasma Physics Reports, 2012, vol. 39, No. 9, pp. 763-767.

An RGF Residential/Commercial Product, Guardian Air™, An RGF PHI™ Technology, as early as Feb. 20, 2015.

Munter, "Advanced Oxidation Processes—Current Status and Prospects", Proc. Estonian Acad. Sci. Chem., 2001, vol. 50, No. 2, pp. 59-80.

PhotoCatalytic Air Purifier, as early as Feb. 20, 2015, 5 pages.

"$TiO_2$ Nanostructures: Recent Physical Chemistry Advances", J. Phys. Chem., C 2012, vol. 116, pp. 11849-11851.

Sias, "Biological Organism Reduction with Hydrogen Peroxide", Controlled Environments, Dec. 31, 2002, 13 pages.

\* cited by examiner

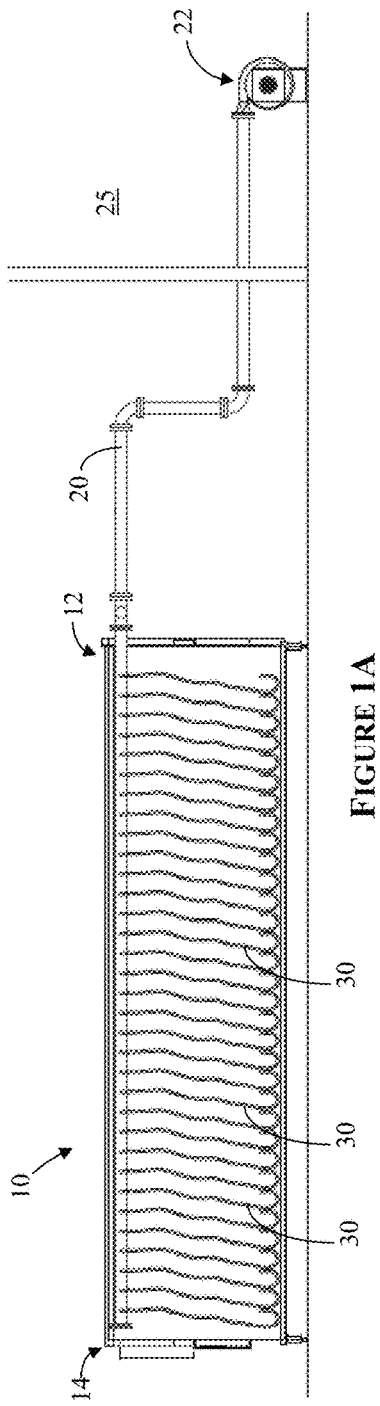
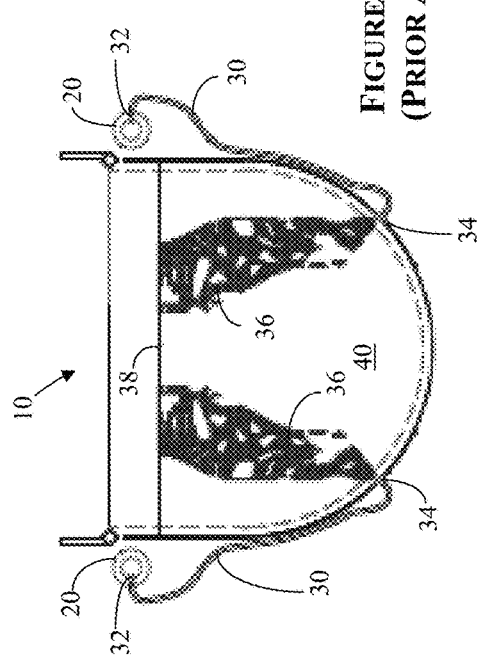
FIGURE 1A (PRIOR ART)
FIGURE 1B (PRIOR ART)

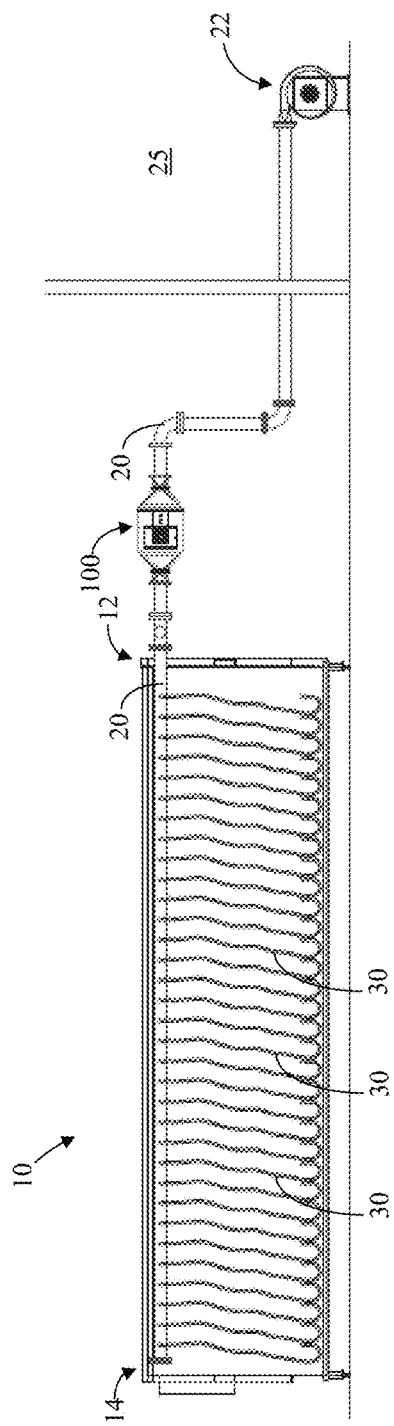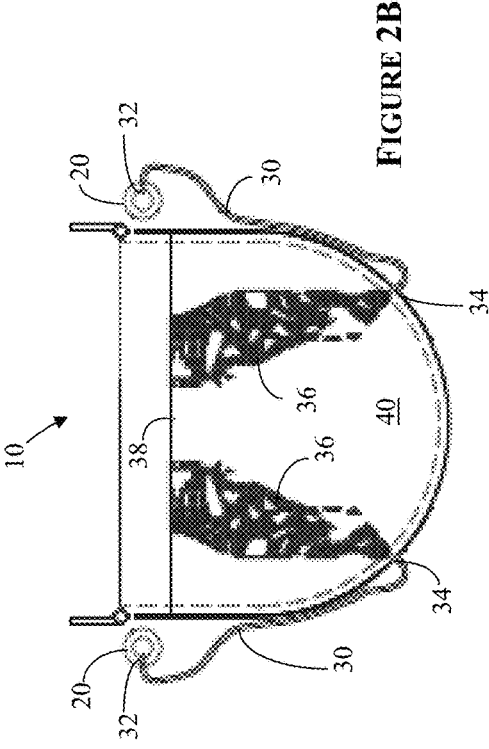
FIGURE 2A
FIGURE 2B

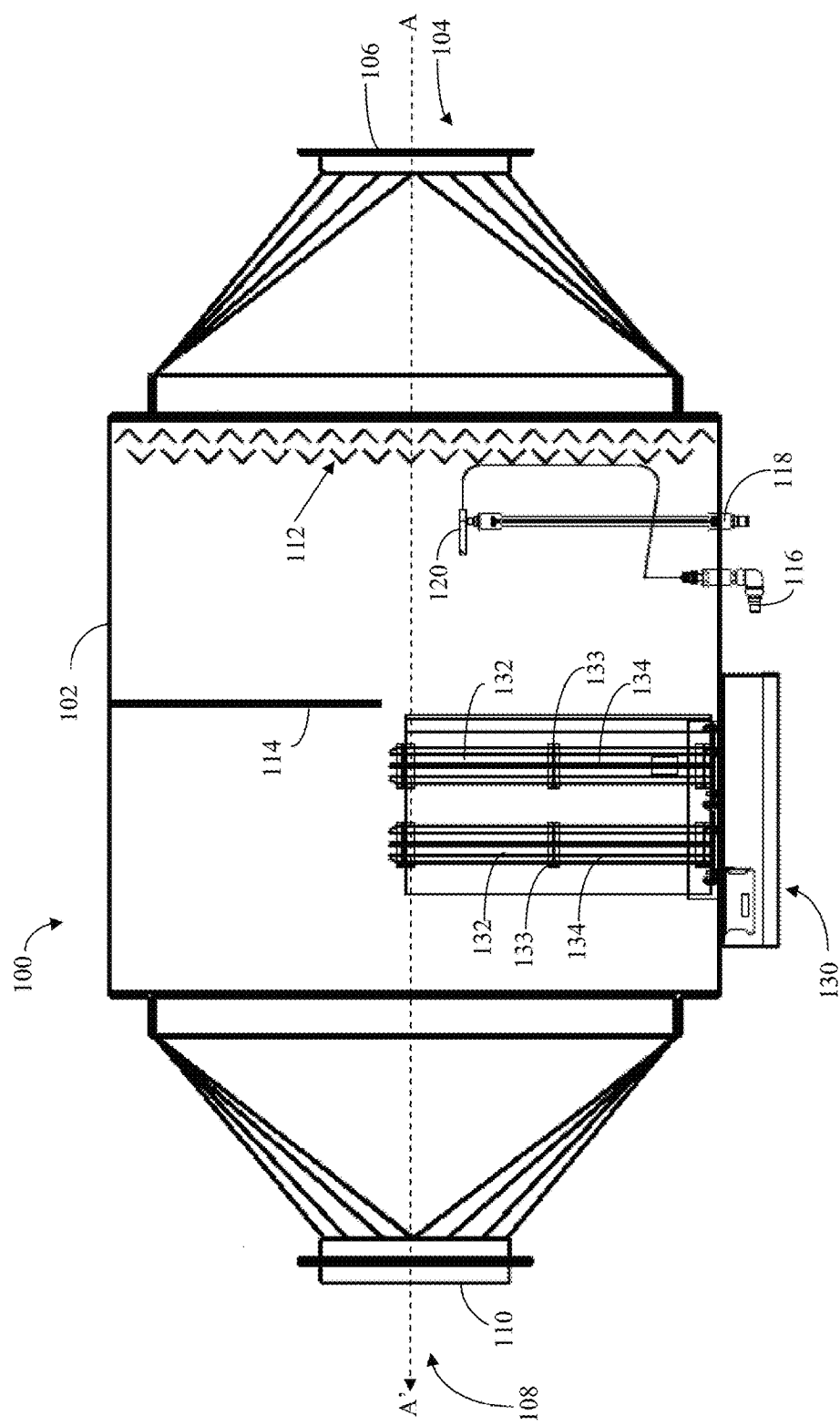

AIR SANITATION APPARATUS FOR FOOD PROCESSING TANKS HAVING AIR AGITATION PIPING AND METHODS THEREOF

RELATED APPLICATION

The present application claims the benefit of U.S. Provisional Application No. 62/097,951, filed Dec. 30, 2014, which is hereby incorporated herein in its entirety by reference.

FIELD OF THE INVENTION

The present invention relates to a process of providing an antimicrobial agent into the air lines that feed into a food processing tank, in some aspects a chiller tank intended for the chilling of protein-based and non-protein-based food products, which helps control microbial growth, prepares the product for further processing and packing/packaging, and/or extends the usable time between filling and draining operations for any soaking, dipping, quenching, rinsing, washing, cooling, heating, or any other antimicrobial treatment in a processing tank in which a product intended for human consumption is processed, and in the case of a chiller tank lowers product temperature. In particular, the present invention relates to an air sanitation apparatus capable of providing an antimicrobial agent in the form of a gas or mist into the air lines that feed into a food processing tank, particularly a chiller tank, more particularly a chiller tank for poultry processing.

BACKGROUND OF THE INVENTION

The world population has grown to point where mass production of the foods that we consume is no longer a luxury but a requirement. Local farmers, providing food and food products directly to the marketplace, cannot meet the demands of modern society. The food supply chain now incorporates very large, complex farms and high speed and very high volume processing plants to satisfy the need for mass processing and production of food. Maintaining a safe food supply chain relies on the dedication of those working in the supply chain, the processing plants, and also on the third party oversight of various federal agencies whose regulations support and mandate food safety.

With two major exceptions, the physical process of taking an animal from the farm to the consumer has changed very little over time. The introduction of refrigeration, and the implementation of various chemistries to help maintain sanitary conditions and to control microbiology, has given modern food processors an advantage not enjoyed by food producers of a century ago. Refrigeration and chemical intervention practices have become an integral part of food processing facility operations. These technologies have enabled the high speed, high volume output of the large processing facilities that could not have been possible in times past without significant concern for consumer safety. With large scale and continuous processing methods being employed by large processors of protein products, or any other product that is susceptible to microbiological contamination, the concern for the control of microbiology and the safety of the food supply chain is of paramount importance.

Another concern, as the demand for food products increases, is the impact on natural resources created by this demand. The ecological impact is directly affected by this growth and therefore new processes must be developed to reduce the impact any given process has on the environment. The ecological impact that a food processing plant has on the environment is no longer a passing concern but a major part of operations and planning. Entire processes are built around the control and conservation of natural resources such as water. Older, outdated and less efficient processes are being replaced at significant cost with more efficient and less wasteful processes that maximizes the utility of available resources. No longer can a plant operate without concern for the conservation and sustainability of natural resources.

Still another concern in slaughtering and processing plants is unwanted airborne microorganisms that are emitted when an animal is processed, such as poultry (i.e., turkey, duck and chicken) during shackling, killing, scalding, and picking areas. These airborne microorganisms are unwanted in the processing and packing areas of the plant because they can affect product quality and safety. They also pose a potential threat to the health and well-being of the workers in the plant. Still further, such airborne microorganisms can affect down-field processes in a processing plant, posing quality and safety concerns.

To insure that the food supply chain in modern society is maintained at the highest levels of safety for the consumer, the plant's employees, and the overall environment, there are federal agencies that monitor the processors operations so that a continually safe food supply is assured and the environmental impact and utilization of natural resources is as safe and efficient as possible. Modern food processing methods are scrutinized by government agencies to ensure compliance with safe handling and processing guidelines designed to minimize issues of food safety in the supply chain. Regulations and routine inspections of systems and processes by federal agencies such as the USDA, EPA and OSHA, mandate a government-industry alliance that helps ensure that every effort is made to deliver the safest for product possible to the consumer.

Very innovative approaches to the systems and methods used in processing facilities have been implemented to create profits for industry while maintaining low consumer cost of the final product. As new processes are developed, the federal agencies that have jurisdiction over any particular process are called upon to review the new approach and to ensure that the new innovation meets the current guidelines for safety. The higher the processors output, the higher the risk of microbiological contamination, and therefore the more innovative the processor must be to combat this ever present threat to the food chain safety. As new risks are found, federal guidelines become more stringent.

Large scale refrigeration systems, used to help control microbial growth in various processing applications, have helped the food processing industry to remain in compliance with food safety goals. Refrigeration applications and processes are implemented at various locations in the processing operation to ensure maximization of microbiology control and shelf life. Depending on the particular product being processed—beef, pork, poultry and fish for example—and the particular operation taking place, various methods of achieving this reduction in product temperature are employed. In poultry processing for example, submersion in large chilled water baths is the allowed and preferred method for the rapid reduction in carcass temperature after evisceration. Other means of accomplishing the reduction in temperature for beef or pork products are utilized that do not currently utilize a large chilled water bath for the purpose.

In industrial processing of poultry, immediately after slaughter, bleeding, hot water immersion, feather withdraw and viscera withdrawal, poultry carcasses have to be chilled to reduce their temperature from approximately 40 to 4° C., which contributes to ensuring safe products. Immersion chilling is a relatively low cost and fast cooling technique largely used in South America and North America in countries such as the United State and Brazil, two of the biggest poultry producers in the world. In this system, poultry carcasses are forced to move through stainless steel tanks containing chilled water or a mixture of ice and water. Water in the system may be agitated by introducing air into the chiller tank from air intake lines to keep bird carcasses buoyant and roiling in the chiller to ensure an even chill. These tanks may also contain antimicrobial intervention solutions to reduce and control bacteria which may compromise food safety and product shelf life. In these tanks, the carcasses are displaced by means of an endless screw in counter-current with the cooling water flow. The United States poultry industries routinely use this rapid chilling process because the United States Department of Agriculture, Food Safety and Inspection Service, demands the chilling of carcasses below 4.4° C. until 4 hours postmortem to minimize microbial growth and to preserve product quality. The cooling rate is influenced by the size, shape, and fat of the carcass, as well as by the temperature and flow pattern (and stirring level) of water inside the tanks.

The means by which this initial chill operation is accomplished in large production facilities is by feeding a continual flow of product on a belt conveyor into the lead-in section of a large chilled water tank and ensuring that the product is submerged continually, typically with a water temperature set at approximately 34° F.

In one typical method, the process incorporates a large tank fitted with a sectionalized and gated conveyor that provides separate sections where the product is loaded. The gates are mounted on a chain-type conveyor and continually move through the chilled water bath with the gates providing segregation from one load to another. The gates continuously push a load of product through the chilled water bath, from the lead-in section to the lead-out section, at a speed that is designed to provide ample dwell time for the intended cooling purpose. Another method of accomplishing the same material handling operation is the use of a large diameter auger placed in the chiller tank in lieu of the moving gates described above. The auger flights determine the volume of product that can be loaded in each section and the auger rotational speed as well as the total length of the tank determines the dwell time the product will be allowed to remain in the chilled bath.

Immersion chilling has a benefit of an increased "washing effect" which lowers the total microbial load on the birds; however, it is also a potential place for cross contamination to occur. In order to control microbiology in chiller tanks, it is a typical practice to add specialized chemistry to the tanks throughout the processing day. This specialized chemistry is known in the industry as an intervention solution. There are several antimicrobials that are approved and effective for use in the chiller to decrease pathogens, including, for instance, chlorine, peroxyacetic acid, bromine, cetylpyridinium chloride (1-hexadecylpyridinium chloride, CPC), organic acids, trisodium phosphate (TSP), acidified sodium chlorite and chlorine dioxide.

Sanitation in chiller management is critical to product quality and safety. There are many components to the chiller that if not cleaned properly can result in higher microbial load (decreased shelf-life) and higher pathogen-positive birds. Large chilled water baths (i.e., chiller tanks) are routinely cleaned by dumping the chilled water bath solutions within the chiller tank, sanitizing the chiller tank, and re-filling the chiller tank with chilled water and any intervention solution. Beyond cleaning the interior volume of the processing tanks, the large chilled water baths also often require routine cleaning or replacement of the air intake lines, which introduce air into the contents of the chiller tank during operation to stir the contents using air agitation. The air intake lines often use an unfiltered compressed air supply from another location within the processing plant. Thus, the air lines should be regularly cleaned and sanitized, or alternatively replaced, to minimize contamination of the processing tank from the introduction of microbial loads (i.e., mold, yeast and/or bacteria) from the air source into the processing tank and prevent unwanted buildup of microbial loads within the air lines.

As such, there is a need in the industry to efficiently and cost-effectively provide a source of air into the air intake lines of processing tanks that minimizes microbial loads into the processing tanks and/or a build-up of microbial loads within the air intake lines, particularly chiller tanks for poultry processing, which not only are time consuming to clean or replace and a source of lost revenue during the down-time that the chiller tank and/or air intake lines are being cleaned or replaced, but a potential source of higher microbial load (decreased shelf-life) and higher pathogen-positive birds if not properly maintained.

SUMMARY OF THE INVENTION

The present invention is directed at a method of providing an antimicrobial agent into the air lines that are used to air agitate a processing tank, wherein the processing tank can be used for any soaking, dipping, quenching, rinsing, washing, cooling, heating, or any other process and/or treatment in a processing tank in which a product intended for human consumption is processed. In some aspects, the antimicrobial agent is provided into the air lines in the form of a gas or mist.

In some aspects, the present invention is directed at a method of providing an antimicrobial agent in the form of a gas or mist into the air lines of a chiller processing tank, wherein the air lines are used to air agitate the liquid contents within the chiller processing tank during normal operation.

In some other aspects, the present invention is directed at a method of providing an antimicrobial agent in the form of a gas or mist into the air lines of a chiller processing tank, wherein the chiller processing tank is used for poultry processing.

In some aspects, the present invention is directed at an air sanitation apparatus capable of providing an antimicrobial agent in the form of a gas or mist into the air lines that feed into a processing apparatus, such as a processing tank. In some aspects, the air sanitation apparatus is provided between a source of compressed air that is used for supplying compressed air to an air supply header and an air supply tube operably connected to the air supply header and the processing apparatus. In some aspects, the air sanitation apparatus is operably connected to the air supply header, such that the source of compressed air passes through the air sanitation apparatus prior to the air being fed into the processing apparatus. In some aspects, the source of compressed air passing through the air sanitation apparatus reduces a microbial load within the source of compressed air, such that the source of compressed air being fed into the processing apparatus or processing tank from the air supply header for air agitation is not a significant source of microbial contamination.

In some aspects, the air sanitation apparatus of the present invention contains a housing having an air inlet and an air outlet, each of the air inlet and air outlet capable of being operably attached to an air supply header, such that air flows through the air sanitation apparatus from the air inlet operably attached to the air supply header and out of the air sanitation apparatus through the air outlet and back into the air supply header that is operably attached to the air outlet.

In some aspects, the air sanitation apparatus of the present invention contains a housing having an air inlet and an air outlet, the air sanitation apparatus having one or more UV light sources and a catalyst surface located between the air inlet and air outlet of the housing, such that the source of compressed air passing through the air sanitation apparatus is exposed to the wavelengths of one or more UV light sources, the one or more UV light sources being powered by a UV light power supply. In some aspects, the UV light sources comprise one or more photohydroionization cells.

In some aspects, the air sanitation apparatus of the present invention contains an air distributor proximate the air inlet and located upstream in the air flow prior to the one or more UV light sources and the catalyst surface.

In some aspects, the air sanitation apparatus has a supply of an antimicrobial agent and/or a secondary supply of compressed air located upstream in the air flow prior to the one or more UV light sources and the catalyst surface. In some aspects, the supply of the antimicrobial agent and the secondary supply of compressed air are located between the air distributor and the one or more UV light sources and the catalyst surface. In some aspects, the supply of the antimicrobial agent and the secondary supply of compressed air are fed into an atomizer or nebulizer to provide the antimicrobial agent in the form of a mist or gas within the air flow. In some aspects, the atomizer or nebulizer is located between the air inlet and the one or more UV light sources and the catalyst surface.

In some aspects, the air sanitation apparatus provides continual treatment of the source of compressed air fed into the processing tank. In some aspects, the air sanitation apparatus continually treats the source of air by atomizing or nebulizing the source of the antimicrobial agent upstream from the UV light sources, which in some aspects comprise one or more photohydroionization cells.

In some aspects, the catalyst surface is positioned in close proximity to the one or more UV light sources emitting energy at a specific wavelengths set to maximize the process effect. In some aspects, the one or more UV light sources contain bands that wrap around the outer surface of the UV light source and/or longitudinal strips that run the length of the UV light source, wherein the catalyst surface is located on the bands and/or longitudinal strips. In some other aspects, the catalyst surface is positioned on a catalyst surface means for being exposed to the air stream, such as strips, a webbing, a filter, or other configurations in the air stream as air passes by the UV light source.

In some aspects, the air sanitation apparatus contains at least two UV light sources, wherein the UV light sources are configured generally parallel to each other within the housing.

In some aspects, the catalyst surface is positioned in close proximity to the one or more UV light sources emitting energy at a specific wavelengths set to maximize the process effect. In some aspects, the one or more UV light sources contain bands that wrap around the outer surface of the UV light source and/or longitudinal strips that run the length of the UV light source, wherein the catalyst surface is located on the bands and/or longitudinal strips.

In some other aspects, the air sanitation apparatus has a catalyst surface located between two adjacent UV light sources. In some aspects, the catalyst surface is provided on a panel that can be inserted between two adjacent UV light sources, the panel capable of being removed from the housing and replaced with a different panel. In some aspects, the panel has a plurality of apertures and/or comprises an air distributor, such that at least a portion of the air flow can pass through the panel.

In some aspects, the one or more UV light sources extend a portion of the housing, the air sanitation apparatus also having an air deflector, such that the source of compressed air passing through the air sanitation apparatus is exposed to the one or more UV light sources. In some other aspects, the one or more UV light sources extend substantially the entire width of the housing, such that the source of compressed air passing through the air sanitation apparatus is exposed to the one or more UV light sources.

In some aspects, the source of the antimicrobial agent is a liquid before being converted to mist or gas. In some aspects, the liquid antimicrobial agent preferably comprises hydrogen peroxide. In some other aspects, the liquid antimicrobial agent preferably comprises a peroxycarboxylic acid. In still some other aspects, the liquid antimicrobial agent comprises chlorine, bromine, cetylpyridinium chloride (CPC), an organic acid, a peroxycarboxylic acid, hydrogen peroxide, trisodium phosphate (TSP), acidified sodium chlorite, chlorine dioxide, and/or mixtures thereof.

In some aspects, the liquid antimicrobial agent comprises at least one peroxycarboxylic acid having 2-18 carbon atoms. In some aspects, the peroxycarboxylic acid solution is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof. Preferably, the antimicrobial agent comprises an equilibrium peroxycarboxylic acid or a pH modified peroxycarboxylic acid.

In some aspects, the equilibrium peroxycarboxylic acid preferably has a pH above about 3.0 and below about 7.0, in some aspects about 3.5 to about 5.5, and in some other aspects about 3.5 to about 5.0, although subranges within these ranges is contemplated. In some preferred aspects, the equilibrium peroxycarboxylic acid comprises peroxyacetic acid.

In some aspects, the pH modified peroxycarboxylic acid preferably has a pH above about 7.0 and below about 10.0, in certain aspects a pH range of about 7.0 to about 9.5, and in some other aspects a pH range of about 7.5 to about 9.0, although subranges within these ranges is contemplated. The pH modified peroxycarboxylic acid can be prepared by combining a peroxycarboxylic acid solution, such as a peroxyacetic acid solution, with one or more buffering agents chosen from sodium hydroxide, potassium hydroxide, the sodium salt and/or the potassium salt of carbonic acid, phosphoric acid, silicic acid or mixtures thereof, in a quantity that is necessary to bring the solution to said pH range One of ordinary skill in the art will appreciate that other alkalizing chemistries approved for direct food contact may also be used, whether alone or in combination with any of the foregoing buffering agents. The quantity of the buffering agent in a buffered peroxycarboxylic acid solution will generally be in the range of about 0.01% to about 10% by volume of the total solution, but other volumes of the buffering agent may be utilized depending upon various parameters, such as local water condition, including pH, hardness and conductivity. In some preferred aspects, the pH modified peroxycarboxylic acid comprises peroxyacetic acid.

In some aspects, the liquid antimicrobial agent is atomized or nebulized into the air flow in the form of a mist or gas having about 0.5 to about 10 micron droplets, in some aspects about 1 to about 9 micron droplets, in some other aspects about 4 to about 7 micron droplets. One of ordinary skill in the art will appreciate that the atomizer/nebulizer can provide desired size droplets of the antimicrobial agent for purposes of the present invention.

BRIEF DESCRIPTION OF THE DRAWINGS

FIG. 1A is a side view of a representative prior art processing tank, particularly a chiller tank used for poultry processing, wherein compressed air is supplied to a compressed air supply header, the compressed air supply header feeding a plurality of tubes spaced apart along the operational length of the processing tank, each of the plurality of tubes operably coupled to a bottom portion of the processing tank, such that compressed air is supplied from each of the plurality of tubes into the interior volume of the processing tank to agitate the liquid contents of the processing tank during normal operation.

FIG. 1B is a cross-sectional view of the representative prior art processing tank of FIG. 1A, further illustrating compressed air being supplied from a compressed air supply header located on each side of the processing tank to a tube that is operably coupled to a bottom portion of the processing tank, such that compressed air is supplied from each of the plurality of tubes into the interior volume of the processing tank to agitate the liquid contents of the processing tank during normal operation.

FIG. 2A is a side view of an air sanitation apparatus according to certain embodiments of the present invention, the air sanitation apparatus inserted in the compressed air supply line of a processing tank, particularly a chiller tank used for poultry processing, wherein sanitized, compressed air is supplied to a compressed air supply header feeding a plurality of tubes spaced apart along the operational length of the processing tank, each of the plurality of tubes operably coupled to a bottom portion of the processing tank, such that the sanitized, compressed air is supplied from each of the plurality of tubes into the interior volume of the processing tank to agitate the liquid contents of the processing tank during normal operation.

FIG. 2B is a cross-sectional view of the processing tank of FIG. 2B, further illustrating sanitized, compressed air being supplied from a compressed air supply header located on each side of the processing tank to a tube that is operably coupled to a bottom portion of the processing tank, such that the sanitized, compressed air is supplied from each of the plurality of tubes into the interior volume of the processing tank to agitate the contents of the processing tank during normal operation.

FIG. 3 is a partial cross-sectional view of an air sanitation apparatus according to certain embodiments of the present invention.

DETAILED DESCRIPTION OF THE DRAWINGS

Figure 4:
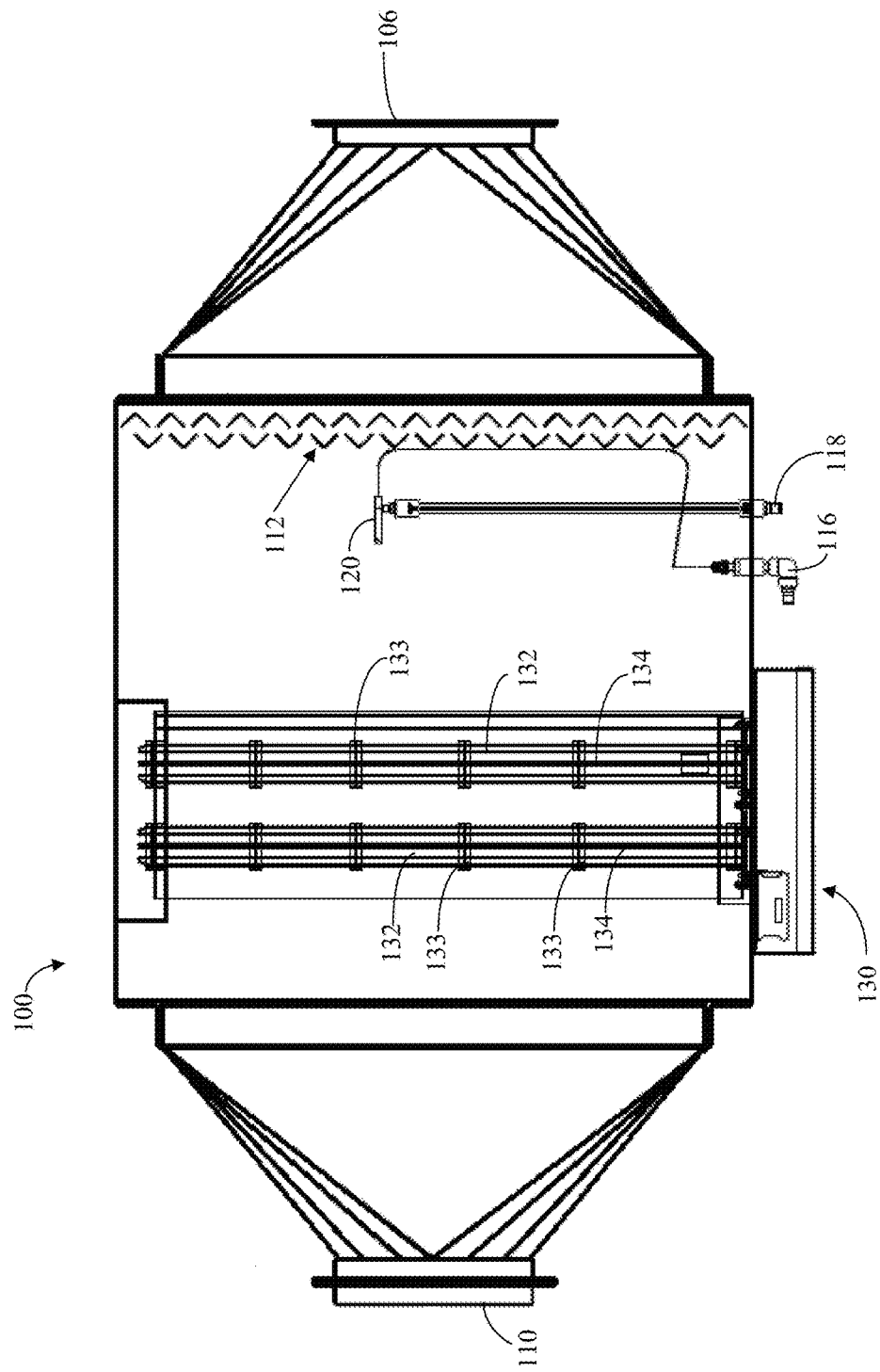
FIG. 4 is a partial cross-sectional view of an air sanitation apparatus according to certain embodiments of the present invention.

Referring generally now to the figures, particularly FIGS. 1A and 1B, is provided a processing tank 10 of the prior art. The processing tank 10 having a product infeed 12 and a product outlet 14, whereby the processing tank 10 contains a bath 40 filled to a desired processing level 38 with a processing liquid, such that the product can undergo any soaking, dipping, quenching, rinsing, washing, cooling, heating, or any other processing in which a product intended for human consumption is processed. During such processing operations, the bath 40 in the processing tank 10 may be stirred by air agitation, which comprises providing sparging bubbles 36 within the bath 40. The air used for air agitation being provided to the processing tank 10 from a compressed air header 20 by the use of a plurality of air agitation tubes 30 that are spaced apart along the longitudinal length of the processing tank 10, the compressed air header 20 being operably connected to a compressed air supply 22, which can be located in another room 25, such as a mechanical room, where the air is unfiltered for microbial loads. The compressed air header 20 can be split into two or more runs, such as shown in FIG. 1B whereby the compressed air header 20 extends the longitudinal length on both sides of the processing tank 10. As illustrated in FIGS. 1A and 1B, the plurality of air supply tubes 30 are operably connected on a proximate end 32 to one of the compressed air headers 20 and to the processing tank 10 on a distal end 34, such that the compressed air flows from the respective compressed air header 20 into the plurality of air agitation tubes 30 and into the processing tank 10 to provide sparging bubbles 36 for air agitation of the bath 40 contained within the processing tank 10.

Referring now to FIGS. 2A and 2B, an air sanitation apparatus 100 of the present invention can be provided in line of the compressed air that is supplied to the processing tank 10. For example, the air sanitation apparatus 100 of the present invention can be operably coupled to a compressed air header 20, such that air flows through the air sanitation apparatus 100 prior to being provided to the processing tank 10. In some aspects, the air sanitation apparatus 100 is provided in line of the compressed air header 20 prior to the compressed air header 20 splitting into two or more compressed air header sections 20, each of the sections 20 substantially traversing a longitudinal length of the processing tank 10. In some other aspects, an air sanitation apparatus 100 can be provided in line of the compressed air header 20 after the compressed air header 20 is split into two sections traversing the longitudinal length of the processing tank 10, such that an air sanitation apparatus 100 can be provided on each section of the compressed air header 20, or only on one such section. The air sanitation apparatus 100 providing an antimicrobial agent in the form of a mist or gas in the compressed air, which is then introduced into the processing tank 10 during the air agitation process.

In some aspects, the bath 40 comprises a chemical intervention solution chosen from chlorine, bromine, cetylpyridinium chloride (CPC), an organic acid, a peroxycarboxylic acid, trisodium phosphate (TSP), acidified sodium chlorite, and chlorine dioxide. The antimicrobial agent is preferably chosen such that it does not interfere with the chemical intervention solution. In some other aspects, the antimicrobial agent may be chosen to further enhance or extend the effectiveness of the bath 40 containing the chemical intervention solution.

Figure 5:
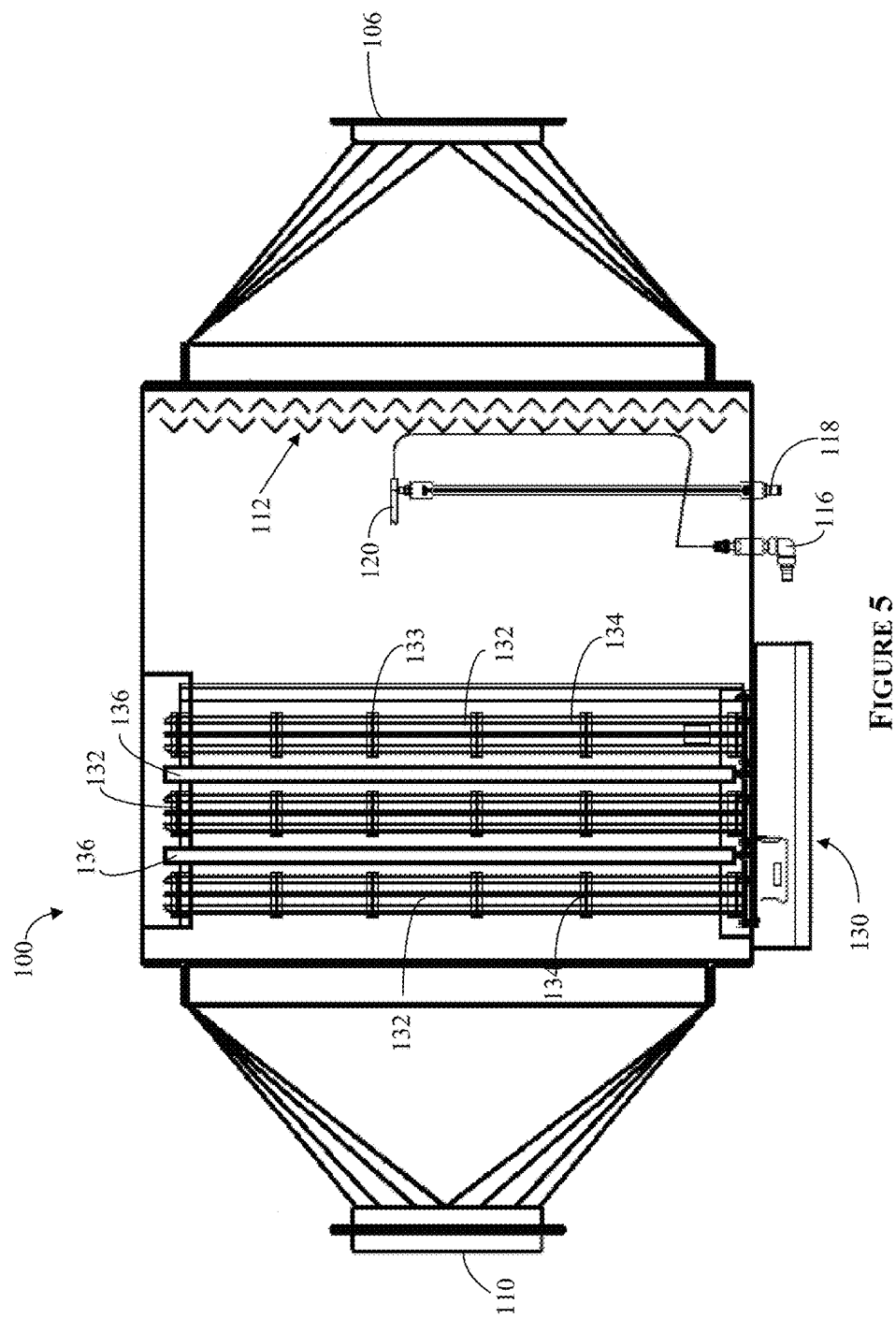
FIG. 5 is a partial cross-sectional view of an air sanitation apparatus according to certain embodiments of the present invention.

Referring now to FIGS. 3-5, the air sanitation apparatus 100 of the present invention contains a housing 102 having an air inlet 104 that may have an air inlet coupling 106 to operably connect the air sanitation apparatus 100 to an upstream section of the compressed air header 20 and an air outlet 108 that may have an air outlet coupling 110 to operably connect the air sanitation apparatus 100 to a downstream section of the compressed air header 20.

Within the housing 102 is comprised one or more UV light sources 132 and a catalyst source, the catalyst source providing a catalyst surface located between the air inlet 104 and air outlet 108, such that the source of compressed air passing through the air sanitation apparatus 100 is exposed to the radiation of the one or more UV light sources 132. The one or more UV light sources 132 being powered by a UV light power supply 130. In some aspects, the UV light sources comprise one or more photohydroionization cells.

While the UV light sources 132 are shown in a generally parallel configuration, the UV light sources may also be provided in an intersecting or criss-cross configuration with respect to each other within the housing. In some aspects, the catalyst surface is positioned in close proximity to the one or more UV light sources 132 emitting energy at a specific wavelengths set to maximize the process effect. In some aspects, the one or more UV light sources 132 contain bands 133 that wrap around the outer surface of the UV light source and/or longitudinal strips 134 that run the length of the UV light source, wherein the catalyst surface is located on the bands 133 and/or longitudinal strips 134 in close proximity to the respective UV light source 132.

An air distributor 112 can also be provided within the housing 102 proximate the air inlet 104 and located upstream in the compressed air flow prior to the one or more UV light sources 132 and the catalyst surface. The air distributor 112 can comprise a baffle, such as an S-shaped or V-shaped baffle, to capture and remove unwanted contaminants in the compressed air flow, such as oil or grease particulate emissions.

Located between the one or more UV light sources 132 and the air inlet 104 is a means 120 for producing the antimicrobial agent in the form of a mist or gas, such as an atomizer or nebulizer, which is fed a source of compressed air 116 and a source of an antimicrobial agent 118. In certain aspects, means 120 for producing the antimicrobial agent in the form of a mist or gas is located between the air distributor 112 and the one or more UV light sources 132 and the catalyst surface. The source of compressed air 116 and the source of an antimicrobial agent 118 are fed into means 120, such as an atomizer or nebulizer, to continually provide the antimicrobial agent in the form of a mist or gas within the air flow prior to the air flow being exposed to the radiation of the UV light sources 132 and the catalyst surface. In some aspects, the air sanitation apparatus 100 continually treats the source of air by atomizing or nebulizing the source of the antimicrobial agent upstream from the UV light sources 132, which in some aspects comprise one or more photohydroionization (PHI) cells.

The catalyst surface is preferably positioned in close proximity to the one or more UV light sources 132 emitting energy at one or more specific wavelengths set to maximize the process effect. In some aspects, the one or more UV light sources 132 contain bands 133 that wrap around the outer surface of the UV light source 132 and/or longitudinal strips 134 that run the length of the UV light source 132, wherein the catalyst surface is deposited or otherwise located on the bands 133 and/or longitudinal strips 134.

During normal operation, the liquid antimicrobial agent is preferably formed into a mist or gas such that the mist or gas of the antimicrobial agent is provided in about 0.5 to about 10 micron droplets, in some aspects about 1 to about 9 micron droplets, in some aspects about 2 to about 8 micron droplets, and in some other aspects about 4 to about 7 micron droplets, with one of ordinary skill in the art appreciating that am atomizer/nebulizer can provide desired size droplets of the antimicrobial agent.

As shown in FIG. 3, the UV light sources 132 may only traverse a portion of the interior width of the housing 102. In such configurations, an air deflector 114 may be utilized to direct the air flow, such that the air flow passes over, under and/or around the area of the UV light sources 132. In some other aspects, as shown in FIGS. 4 and 5, the one or more UV light sources 132 extend substantially the entire width of the housing 102, such that the source of compressed air passing through the air sanitation apparatus 100 is exposed to the one or more UV light sources 132.

In certain aspects, the catalyst surface can be located between two adjacent UV light sources 132. In some aspects, as shown in FIG. 5, the catalyst surface can be provided on one or more panels 136 that can be inserted between two adjacent UV light sources 132, each panel 136 capable of being removed from the housing 102 and replaced with a different panel 136, depending upon the catalyst surface reaching its lifetime, becoming contaminated, being replaced with a different catalyst, or the like. In some aspects, the panel 136 having the catalyst surface has a plurality of apertures or comprises an air distributor, such that the air flow can pass through the panel 136 during normal operation.

Prior to being fed into the means 120 for producing the antimicrobial agent in the form of a mist or gas, the source of the antimicrobial agent 118 is a liquid. In some aspects, the liquid antimicrobial agent preferably comprises hydrogen peroxide. In some other aspects, the liquid antimicrobial agent preferably comprises a peroxycarboxylic acid. In still some other aspects, the liquid antimicrobial agent comprises chlorine, bromine, cetylpyridinium chloride (CPC), an organic acid, a peroxycarboxylic acid, hydrogen peroxide, trisodium phosphate, acidified sodium chlorite, chlorine dioxide, and/or mixtures thereof.

In some aspects, the liquid antimicrobial agent comprises hydrogen peroxide. By providing micron-sized droplets of hydrogen peroxide in the compressed air source, there are more available free radical hydroxyls to perform the desired work of sanitizing the compressed air stream. In certain aspects, the hydrogen peroxide is provided at a concentration in a range of about 3% to about 50%, in some other aspects about 5% to about 35%, and in some other aspects about 5% to about 10%.

In some aspects, the liquid antimicrobial agent comprises at least one peroxycarboxylic acid having 2-18 carbon atoms. In some aspects, the peroxycarboxylic acid solution is chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof. Preferably, the antimicrobial agent comprises an equilibrium peroxycarboxylic acid or a pH modified peroxycarboxylic acid.

In some aspects, the equilibrium peroxycarboxylic acid preferably has a pH above about 3.0 and below about 7.0, in some aspects about 3.5 to about 5.5, and in some other aspects about 3.5 to about 5.0, although subranges within these ranges is contemplated. In some preferred aspects, the equilibrium peroxycarboxylic acid comprises peroxyacetic acid.

In some aspects, the pH modified peroxycarboxylic acid preferably has a pH above about 7.0 and below about 10.0, in certain aspects a pH range of about 7.0 to about 9.5, and in some other aspects a pH range of about 7.5 to about 9.0, although subranges within these ranges is contemplated. The pH modified peroxycarboxylic acid can be prepared by combining a peroxycarboxylic acid solution, such as a peroxyacetic acid solution, with one or more buffering agents chosen from sodium hydroxide, potassium hydroxide, the sodium salt of carbonic acid, the potassium salt of carbonic acid, phosphoric acid, silicic acid or mixtures thereof, in a quantity that is necessary to bring the solution to said pH range One of ordinary skill in the art will appreciate that other alkalizing chemistries approved for direct food contact may also be used, whether alone or in combination with any of the foregoing buffering agents. The quantity of the buffering agent in a buffered peroxycarboxylic acid solution will generally be in the range of about 0.01% to about 10% by volume of the total solution, but other volumes of the buffering agent may be utilized depending upon various parameters, such as local water condition, including pH, hardness and conductivity. In some preferred aspects, the pH modified peroxycarboxylic acid comprises peroxyacetic acid.

The catalyst surface preferably substantially surrounds the UV light source 132. The ultraviolet light emitted from at least one UV light source 132 includes ultraviolet light energy between about 10 nm and about 400 nm, in some other aspects about 50 nm to about 350 nm, and in some other aspects about 100 nm to about 300 nm. In some aspects, the catalyst surface comprises titanium dioxide. In some other aspects, the catalyst surface comprises a transition metal oxide, such as titanium dioxide. In some aspects, the catalyst surface can comprise two or more transition metal oxides, or transition metal alloy oxides, such as titanium alloyed with iron, aluminium, vanadium, and molybdenum. In some aspects, the catalyst surface can also comprise at least one of the following metallic compounds: silver; copper; and rhodium, if not all three compounds. In some other aspects, the catalyst surface contains silver ions, such as silver dihydrogen salts.

In some aspects, the air sanitation apparatus 100 utilizes a UV/H2O2 Advanced Oxidation Process (AOP). Oxidizers created during advanced oxidation processes are much more effective than traditional oxidants at reacting with compounds such as microbes, odor causing chemicals, and other inorganic and organic chemicals. Oxidants that may be created in an advanced oxidation process are considerably stronger than typical cleaning agents such as chlorine. These oxidants, generally referred to as advanced oxidation product or AOP, include Ozone, Hydroxyl Radicals, Hydro Peroxides, Ozonide Ions, Hydroxides, and Super Oxide ions. All of these compounds are either used during or are produced as a result of advanced oxidation processes. With the process of the present invention, not only is the catalyst surface active, but also is the air space between the catalyst surface and the UV light source 132.

Generally, advanced oxidation product will react with compounds that typically will not react with other common oxidants. An example of one of the strong oxidizers created by advanced oxidation processes is the Hydroxyl Radical. The Hydroxyl Radical (OH—) is very unstable, thereby making it very aggressive for a free radical. One method that creates the Hydroxyl or free radical is when ozone and water react with ultraviolet light energy and protolysis occurs. Although the Hydroxyl Radicals are very short lived, they have a higher oxidation potential than ozone, chlorine, or hydrogen peroxide, and their unstable nature increases their reaction speed. A strong benefit of advanced oxidation is the end product of carbon dioxide and water.

Water found in the processing plant air can be drawn through the air sanitization apparatus of the present invention, where the water is absorbed by a desiccant material. Water can also be introduced into the air sanitization apparatus by the liquid antimicrobial agent that is atomized/nebulized. Once absorbed, the water is brought into contact with the catalyst and exposed to the UV radiation. When this moisture is exposed to UV radiation, and allowed ample time to absorb the UV radiation while retained on the descant material, several processes are initiated.

While in the presence of ultraviolet (UV) light, the $H_2O$ is broken into hydroxyl radicals (.OH). The oxidation potential of a hydroxyl radical (2.8V) is much greater than ozone (2.07V) and chlorine (1.39V) and thus has the capability of oxidizing a variety of organic and inorganic contaminants. The recombination of the hydroxyl and ozone free radicals in the presence of the catalyst, promotes the development of hydrogen peroxide. UV light catalyzes the dissociation of hydrogen peroxide into hydroxyl radicals through chain reactions or the hydrogen peroxide is entrained into the air stream where it destroys bacteria and fungus. This in combination with the dislodged free radicals and the UV radiation means the sanitation system utilizes four different bacteria and/or fungi killing agents in a very safe and effective way.

The combination of safe low level ozone ($O_3$), hydroxyls and a broad spectrum UV light enhanced by a catalyst containing a hydrated quad-metallic compound produces an advanced oxidation reaction. This process also produces hydro-peroxides, super oxide ions, ozonide ions and hydroxides. By providing the proper UV light wavelength, in combination with a triple function, low maintenance unit, the PHI Cell provides safe hydro-peroxides, super oxide ions, ozonide ions and hydroxides to purify the air. PHI is not a typical UV light source placed in an air stream, and it is not a high maintenance open electrode ozone generator.

In some aspects, the air sanitation apparatus of the present invention utilizes the antimicrobial agent, such as hydrogen peroxide, to "seed" the incoming air prior to the PHI cell for a dramatically increase volume of free radical generation. For example, by providing ultra-small droplets of 10% $H_2O_2$ in the incoming air, there are more available free radical hydroxyls to perform the desired work of sanitizing the air stream and/or the food product within the processing tank 10. In some aspects, the specialized nebulizing injector provides about 0.5 to about 10 micron droplets, in some aspects about 1 to about 9 micron droplets, in some aspects about 2 to about 8 micron droplets, and in some other aspects about 4 to about 7 micron droplets of hydrogen peroxide on a continuous basis with the supply delivered to all units through on chemical delivery system positioned in a convenient location. One of ordinary skill in the art will appreciate that the nebulizing injector can provide different sized droplets of hydrogen peroxide depending upon the specific application.

In some aspects, the hydrogen peroxide consumption rate is approximately 0.5 GPM Max with effective flows as low as 2 mL/hr depending on organic loading.

In some other aspects, the liquid antimicrobial agent consumption rate through the means for producing the antimicrobial agent in the form of a mist or gas is approximately 1.9 Liters per minute with effective flow rates as low as 2 mL/hr, depending on organic loading. In some aspects, the liquid antimicrobial agent consumption rate is about 0.5 Liters per minute to about 3.0 Liters per minute. In some aspects, the effective flow is between about 2 mL/hr and about 5 mL/hr. One of ordinary skill in the art will appreciate that the consumption rate is dependent upon unit size, volume of air treated, and operating time per day, such that values outsides these ranges are contemplated.

With the air sanitation apparatus of the present invention, micro-organisms can be reduced up to at least about 80%, in some aspects at least about 85%0% in some aspects at least about 90%, in some aspects at least about 95%, and in some other aspects at least about 99.99% in certain situations. Gases, VOCs and odors can also be reduced significantly, and the plant will contain ozonide ions, hydro-peroxides, super oxide ion and hydroxides which will provide continuous protection for the air as well as equipment without the use of temperamental and very problematic open electrode plasma or corona discharge ozone generation systems.

The invention claimed is:

1. A processing tank sanitation system, comprising:
a compressed air header operably connected to a compressed air supply, wherein the air header includes an in-line air sanitation apparatus located upstream of a plurality of air agitation tubes operably connected to a processing tank, the air agitation tubes spaced apart along a longitudinal length of the processing tank;
wherein the air sanitation apparatus includes a housing having a compressed air inlet and a sanitizing compressed air outlet located downstream of the compressed air inlet, an inlet coupling operably connecting the compressed air inlet to the compressed air header, an outlet coupling operably connecting the sanitizing compressed air outlet to the compressed air header, a UV light source and a vaporizing means located within the housing, the vaporizing means in fluid connection with a compressed air source and a liquid antimicrobial agent source, the compressed air source and the liquid antimicrobial agent source capable of being fed into the vaporizing means to provide the liquid antimicrobial agent in the form of an antimicrobial aerosol to mix with the compressed air supply and form a seeded compressed air stream upstream of the UV light source, wherein the seeded compressed air stream is exposed to the UV light source generating reactive oxygen species to create a sanitizing compressed air stream, the sanitizing compressed air stream having a least a portion of the antimicrobial aerosol; and
the sanitizing compressed air stream exiting the air sanitation apparatus via the sanitizing compressed air outlet and supplied to the processing tank through each of the plurality of air agitation tubes such that sparging bubbles of the sanitizing compressed air stream agitate a chemical intervention solution within the processing tank;
wherein the antimicrobial aerosol does not interfere with the chemical intervention solution within the processing tank for processing a food product.

2. The processing tank sanitation system of claim 1, wherein at least one UV light source comprises a photohydroionization cell.

3. The processing tank sanitation system of claim 1, further comprising an air distributor located within the housing of the air sanitation apparatus proximate to the compressed air inlet and upstream to at least one UV light source.

4. The processing tank sanitation system of claim 1, further comprising two or more UV light sources, wherein a catalyst surface is located proximate each of the two or more UV light sources.

5. The processing tank sanitation of claim 1, wherein the at least one UV light source contains one or more bands that wrap around the outer surface of the UV light source, wherein the catalyst surface is located on at least one of the bands.

6. The processing tank sanitation system of claim 1, wherein the at least one UV light source contains one or more longitudinal strips that run the length of the UV light source, wherein the catalyst surface is located on at least one of the longitudinal strips.

7. The processing tank sanitation system of claim 1, wherein the catalyst surface further comprises a desiccant for absorbing water from the air that is flowing through the air sanitation apparatus.

8. The processing tank sanitation system of claim 1, the apparatus comprising at least two UV light sources configured generally parallel to each other within the air sanitation apparatus.

9. The processing tank sanitation system of claim 1, the apparatus comprising at least two UV light sources configured generally perpendicular to each other within the air sanitation apparatus.

10. The processing tank sanitation system of claim 1, the apparatus comprising at least two UV light sources, wherein the catalyst surface is located between two adjacent UV light sources.

11. The processing tank sanitation system of claim 10, the apparatus comprising a panel located between the two adjacent UV light sources, wherein the catalyst surface is provided on the panel.

12. The processing tank sanitation system of claim 11, wherein the panel comprising the catalyst surface is capable of being removed from the housing and replaced with a different panel.

13. The processing tank sanitation system of claim 1, wherein the liquid antimicrobial agent comprising hydrogen peroxide or a peroxycarboxylic acid.

14. The processing tank sanitation system of claim 13, wherein the liquid antimicrobial agent comprises at least one peroxycarboxylic acid having 2-18 carbon atoms chosen from peroxyformic acid, peroxypropionic acid, peroxyacetic acid, peroxybutanoic acid, peroxypentanoic acid, peroxyhexanoic acid, peroxyheptanoic acid, peroxyoctanoic acid, peroxynonanoic acid, peroxydecanoic acid, peroxyundecanoic acid, peroxydodecanoic acid, peroxylactic acid, peroxymaleic acid, peroxyascorbic acid, peroxyhydroxyacetic acid, peroxyoxalic acid, peroxymalonic acid, peroxysuccinic acid, peroxyglutaric acid, peroxyadipic acid, peroxypimelic acid, peroxysubric acid, and mixtures thereof.

15. The processing tank sanitation system of claim 13, wherein the liquid antimicrobial agent comprises an equilibrium peroxycarboxylic acid or a pH modified peroxycarboxylic acid, the equilibrium peroxycarboxylic acid preferably having a pH above about 3.0 and below about 7.0.

16. The processing tank sanitation system of claim 13, wherein the liquid antimicrobial agent is atomized or nebulized into the compressed air supply in the form of a mist or gas having about 0.5 to about 10 micron droplets.

17. The processing tank sanitation system of claim 1, wherein the processing tank is a chiller processing tank for poultry processing.

18. The processing tank sanitation system of claim 1, wherein the liquid antimicrobial agent comprises peroxyacetic acid.

19. The processing tank sanitation system of claim 1, wherein the liquid antimicrobial agent comprises peroxylactic acid.

20. The processing tank sanitation system of claim 1, wherein the liquid antimicrobial agent is configured to be fed into the vaporizing means at a consumption rate of about 0.5 Liters per minute to about 3.0 Liters per minute.

21. The processing tank sanitation system of claim 1, wherein the liquid antimicrobial agent is configured to be fed into the vaporizing means at a flow rate of about 2 mL/hour and about 5 mL/hour.

* * * * *